United States Patent [19]

Niskin, deceased et al.

[11] Patent Number: 4,852,413

[45] Date of Patent: Aug. 1, 1989

[54] WATER SAMPLER ROSETTE

[76] Inventors: Shale Niskin, deceased, late of Miami Beach; by Deborah E. Niskin, executor, 3415 Chase Ave., Miami Beach, both of Fla. 33140

[21] Appl. No.: 233,014

[22] Filed: Aug. 17, 1988

[51] Int. Cl.$^4$ .............................................. G01N 1/12
[52] U.S. Cl. ............................. 73/864.67; 73/364.63
[58] Field of Search .......................... 73/863.63–863.67

[56] References Cited

U.S. PATENT DOCUMENTS

| | | | |
|---|---|---|---|
| 3,242,740 | 3/1966 | Nisken | 73/864.67 |
| 3,339,417 | 9/1967 | Richards . | |
| 3,489,012 | 1/1970 | Niskin . | |
| 4,037,477 | 7/1977 | Nisken | 73/864.67 |
| 4,593,570 | 6/1986 | Niskin | 73/864.67 |

OTHER PUBLICATIONS

General Oceanics Catalog, pp. 7 and 8.

Primary Examiner—Stewart J. Levy
Assistant Examiner—Robert R. Raevis
Attorney, Agent, or Firm—William A. Newton

[57] ABSTRACT

Disclosed is a water sampler device including a holder, a plurality of water-collecting containers mounted in a circular arrangement around the periphery of the holder, each of the water-collecting containers having a pair of opposed opened portions with each opened portion including a rotatable valve mounted therein, triggering means for rotating the rotatable valves from an initially closed condition to an opened condition and then back to the closed condition to obtain a sample of the water.

17 Claims, 7 Drawing Sheets

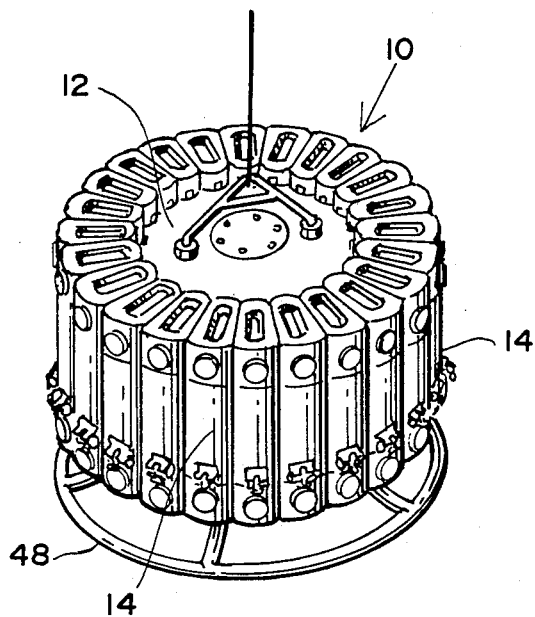
FIG.1
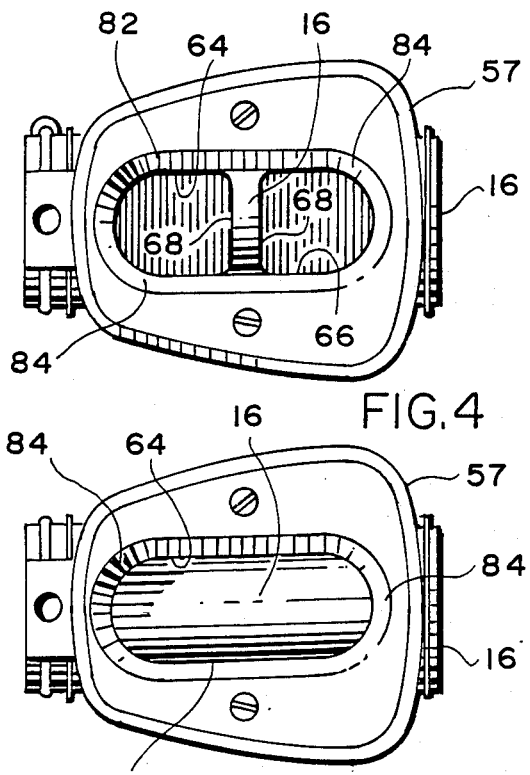
FIG.4
FIG.3
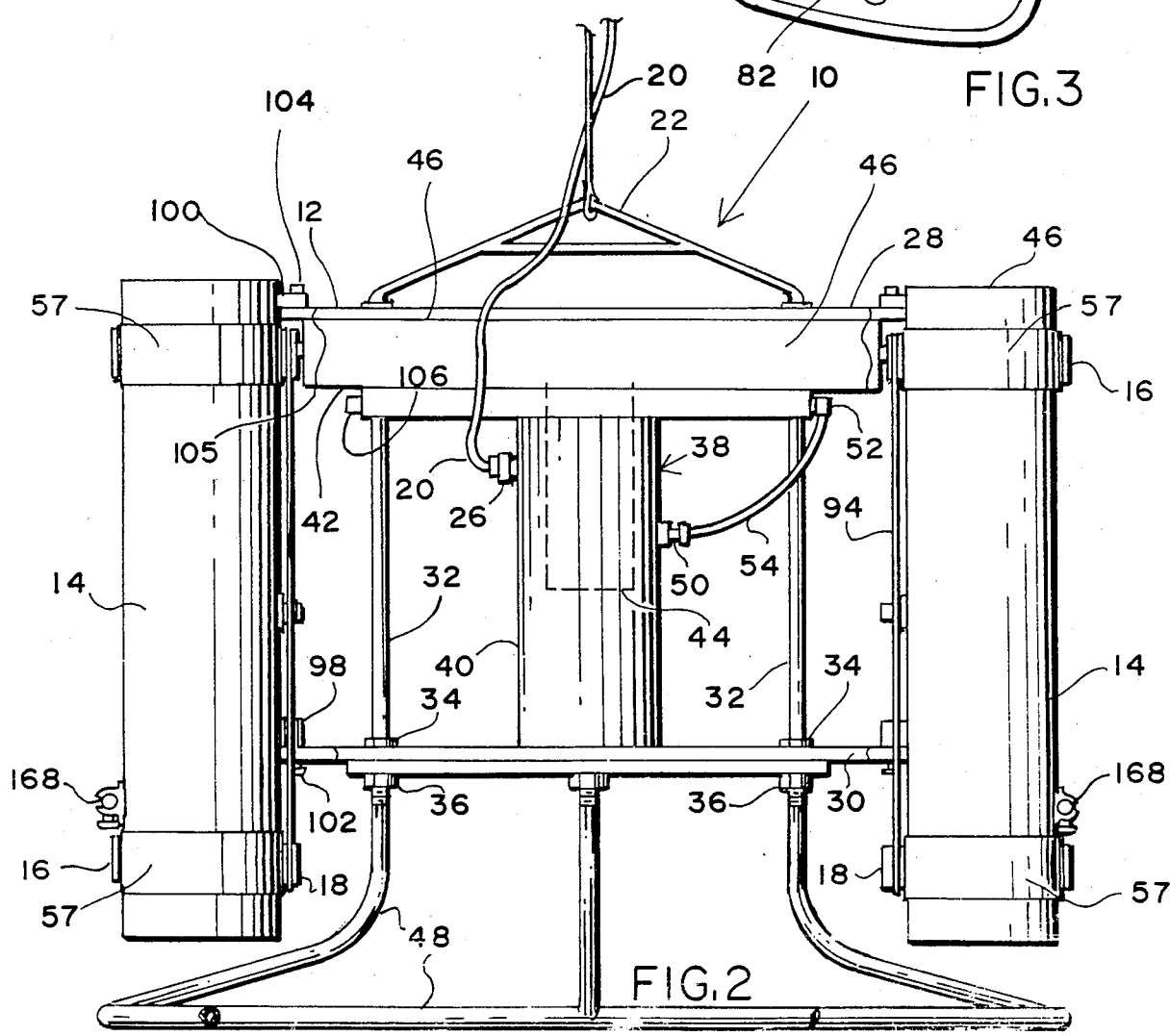
FIG.2

WATER SAMPLER ROSETTE

BACKGROUND OF THE INVENTION

1. Field of the Invention

This invention relates to water sample collecting devices.

2. Description of the Prior Art

Water sampler rosettes are shown in U.S. Pat. Nos. 3,339,417 and 3,489,012. Such rosettes comprise a holder and a plurality of water-collecting containers disposed therearound in a circular arrangement. Additionally, U.S. Pat. No. 4,593,570 discloses a single-water sampling device which, although not adapted for a rosette, is of interest in that it shows the use of ball valves and keys for rotating the same.

Applicant, through his wholly owned corporation, has sold rosettes similar to that shown in U.S. Pat. No. 3,489,012, but being modified to include water-collecting containers having ball valves similar to those in U.S. Pat. No. 4,593,570.

SUMMARY OF THE INVENTION

The present invention is directed to a water-sampler device or rosette comprising a holder and a plurality of water-collecting containers mounted around such holder in a circular arrangement. Each of the water-collecting containers or bottles comprise a tubular member with a pair of opposed, opened end portions with a rotatable valve mounted in each opened end portion.

The first aspect of the present invention comprises a novel triggering mechanism for rotating the pair of rotatable valves from an initially closed condition to a subsequent opened condition and then back to an closed condition to collect a sample of water at a predetermined depth. The triggering means includes an elongated member having a rotation-stopping portion, a central portion, and a spiral rod portion. The rotation-stopping portion includes first and second catch means taking the form of a pair of ledges. With respect to a first longitudinal axis of the rotation-stopping portion, the second catch means is disposed a greater distance from the end of the elongated member and a greater distance from the first longitudinal axis than the first catch member. A rotatable member having a rotational axis is disposed in surrounding relationship to at least a part of the spiral rod portion with the rotational axis of the rotatable member being substantially coincident with a second longitudinal axis of the spiral rod portion. The rotatable member has traversing means which engage opposed sides of the spiral rod portion to cause displacement of the spiral rod portion along the rotational axis of the rotatable member when the rotatable member is rotated. Torque means are provided to apply a torque to the rotatable member. Stop means are mounted to the holder for engaging the first catch means in a first stop position to prevent longitudinal movement of the elongated member along its longitudinal axes and for engaging the second catch means in a second stop position to again prevent further longitudinal movement of the elongated member. Lateral movement means are provided and preferably comprise a solenoid with a plunger to move the rotation-stopping portion laterally with respect to its longitudinal axis and biasing means to limit such lateral movement to a predetermined distance just sufficient to cause the first catch means to clear the stop means and, subsequent to that, to cause the second catch means to clear the stop means.

Once the first catch means is disengaged from the stop means, the rotatable member is no longer prevented from rotating. The rotation of the rotatable member advances the elongated member forward until the second catch means engages the stop means and once again further longitudinal movement of the elongated member is prevented. Coupling means are provided to transfer the rotational movement of the rotatable member to the rotatable valve, so that rotation of the rotatable member permitted by the longitudinal movement of the elongated member between the first stop position and the second stop position allows for the rotatable member to rotate the rotatable valve from its closed position to its opened position. In the same manner, when the lateral movement means causes the second catch means to clear the stop means, the rotatable valve rotates from its opened position to its closed position. Preferably, but not necessarily, joint means are provided in the center protion of the elongated member so as to allow the upward movement of the end of the rotation-stopping portion without affecting the orientation of the second longitudinal axis of the spiral rod portion.

In a second aspect of the invention, each water-collecting container has a cross-sectional configuration of a trapizoid. This unique configuration, which differs from the cylindrical configurations of the prior art, allows for a substantial number of additional water-collecting containers to be mounted around the holder. Additionally, this shape allows the monofilament securing the top casing to go into its grooves better and allows for a better O-ring engagements.

In a third aspect of the invention, a plastic bag is mounted inside of the water-collecting containers.

In a fourth aspect of the invention, a novel drain valve is provided.

BRIEF DESCRIPTION OF THE DRAWINGS

Further objects and advantages of the present invention will become apparent as the following description proceeds, taken in conjunction with the accompanying drawings in which:

FIG. 1 shows a perspective view of the water sampling device of the present invention.

FIG. 2 shows a side view of the water sampler device of the present invention.

FIG. 3 shows a top view of the bottles of the present invention with the cylindrical valve closed.

FIG. 4 shows a top view of the bottles of the present invention with the cylindrical valve opened.

DETAILED DESCRIPTION OF THE PREFERRED EMBODIMENT

Figure 5:
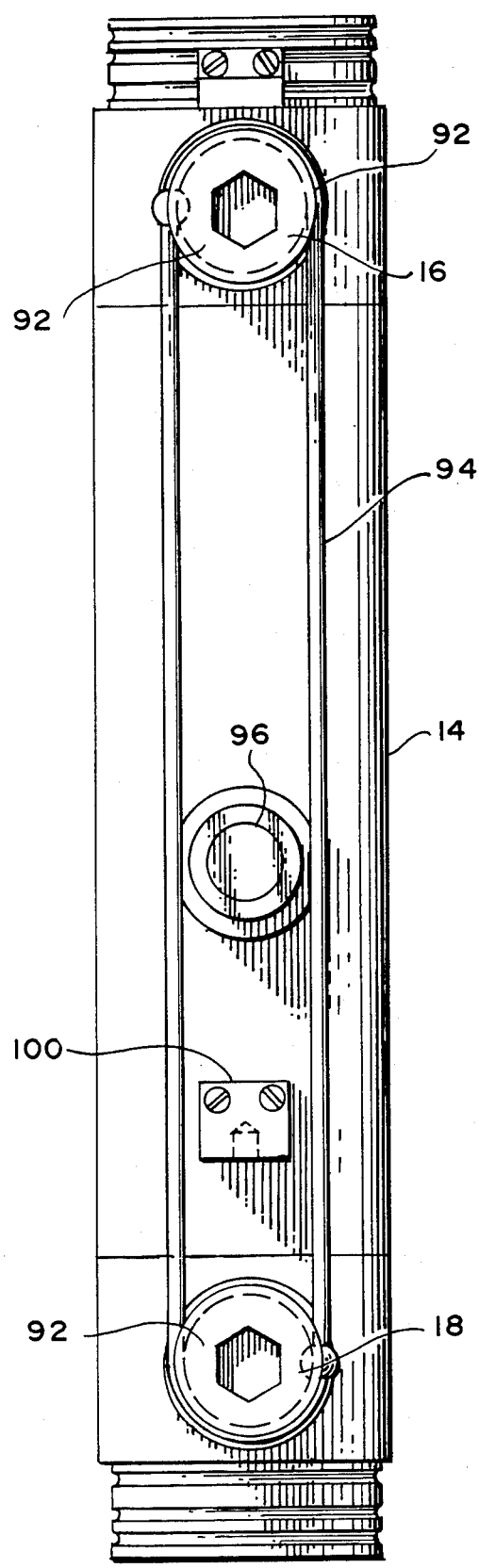
FIG. 5 shows a side view of one of the bottles of the present invention.
Figure 6:
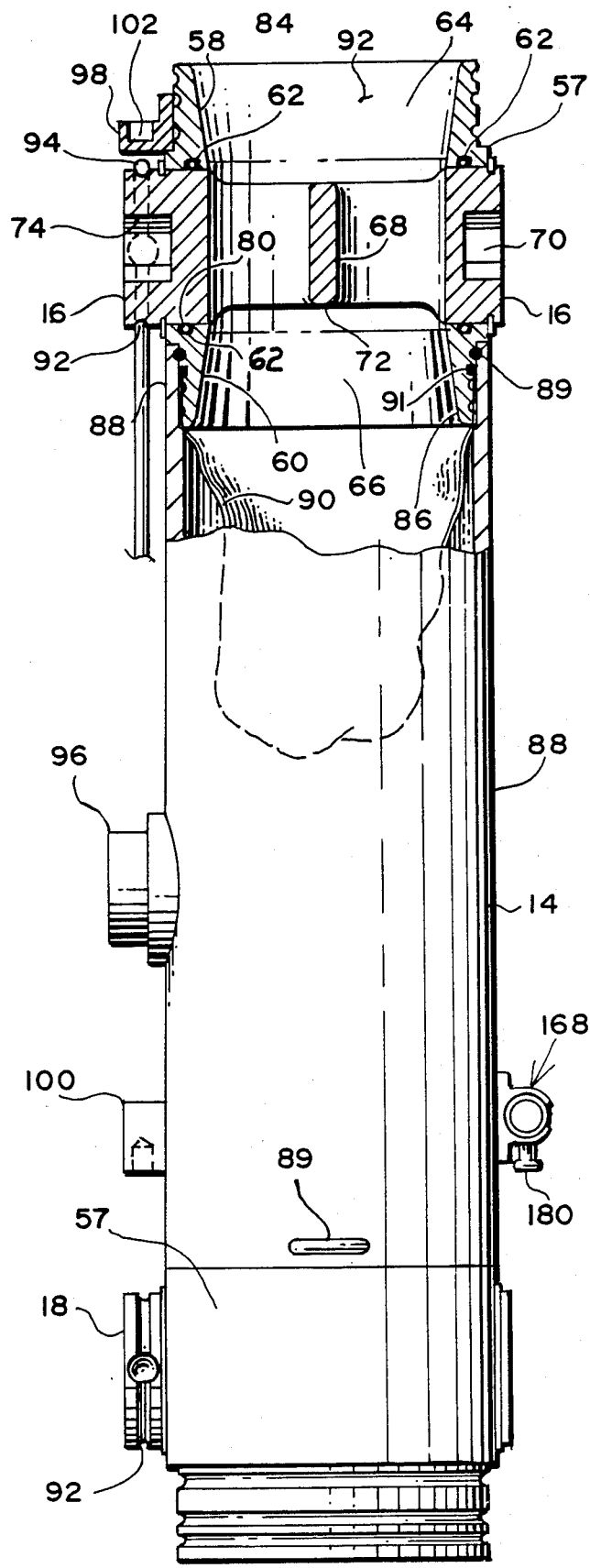
FIG. 6 shows a partially cut away view of one of the bottles of the present invention.

Referring to the FIGS. 1 and 2, wherein like numerals are used to designate similar parts throughout the several views, the numeral 10 refers to a water sampling device which includes a holder 12 on which a plurality of water-collecting containers, i.e., sampler bottles 14 are mounted. Referring to FIGS. 3 through 7, each of the sampler bottles 14 include a pair of opposed cylindrical valves 16 and 18 positioned at each end and capable of rotating from closed to opened, and then opened to closed positions, similar to that shown in U.S. Pat. No. 4,593,570. As shown in FIGS. 1 and 2, lowering power cable 20 is connected to the water sampling device 10 so that it can be lowered into the water. As certain depth are reached, the water sampling device is triggered so that selected sampler bottles 14 collect the water at the selected depth. As shown in FIGS. 5 and 6, the cylindrical valves 16 and 18 rotate to their closed position so as to create a sealed sample. When the device 10 is brought up to the surface, the device 10 will have mounted thereon a plurality of sealed bottles 14 containing samples of water from known and predetermined depths.

Referring to FIG. 2, the water sampler device 10 is connected to the power cable 20 by fastening members 22. Along the center of the power cable 20 there extend insulated electrical conductors which project beyond the end of the power cable 20 into the holder 12. The cable 20 is secured to the holder 12 by a coupling 26. The holder 12 includes a pair of opposed disc-shaped plates 28 and 30 secured in spaced-apart relationship by a plurality of rods 32. Each rod 32 has threaded ends and an enlarged portion 34 which abuts against the plates 28 or 30 with a nut 36 securing the rod on the other side of the plate. The fastening member 22 comprises two rods formed in the shape of a flattened "A" secured to the top plate 28. The holder 12 has a housing 38 having a cylindrical, elongated center position 40 and an upper, peripheral cylindrical upper portion 42. A power supply and electronic module 44 is contained within the center portion 40. A plurality of triggering mechanisms 46 for activating the cylindrical valves 16 is partly contained within the upper portion 42. A frame 48 is securely bolted to the lower plate 30 and is used as a stand for supporting the holder 12 and bottles 14 when it is sitting on a flat surface, such as before and after the water sampler device 10 is lowered into the water. A pair of electrical connectors 50 and 52 are coupled to the center portion 40 and upper portion 42, respectively. A conduit 54 extends between the connectors and contains electrical conductors (such electrical conductors being identified by numeral 56 in FIG. 8).

As can be seen from the top view of the water sampler device 10 in FIG. 2, a plurality of bottles 14 are removably mounted to the periphery of the opposed plates 28 and 30. In the preferred embodiment, there are 36 bottles 14, although the number of bottles may be varied, depending upon the application. Referring to FIG. 6, each bottle 14 includes the pair of opposed cylindrical valves 16 and 18 positioned at each end of the bottle 14. Each cylindrical valves 16 or 18 is secured at the periphery by a cylindrical casing 57. Each cylindrical casing 57 defines integrally formed outer seat 58 and inner seat 60, one of the seats being on each side of the valve. One of a pair of ring-shaped gaskets 62 is positioned at each end of the valve 16 in grooves formed in the seats. The seats 58 and 60 define a pair of axially located apertures 64 and 66 respectively. The cylindrical valve 16 has a pair of apertures 68 (although one is sufficient) which align with the apertures 64 and 66 when the valve 16 or 18 is in its opened position. With 90° rotation, the valve 16 rotates from a closed position shown in FIG. 3 to an opened position shown in FIG. 4 and then with another 90° rotation, the valve 16 rotates from its opened position to its closed position. In the preferred embodiment the valves 16 and 18 are initially set in a closed position, and upon reaching the desired depth, they are rotated 90° to their opened position. After obtaining the water sample, they are again rotated 90° to their close position. For other applications, it may be desirable to have the valve initially in an opened position so as to wash out the sampler. To the extent so far described, the valve 18 on the other end of the bottle 14 is identical.

Figure 7:
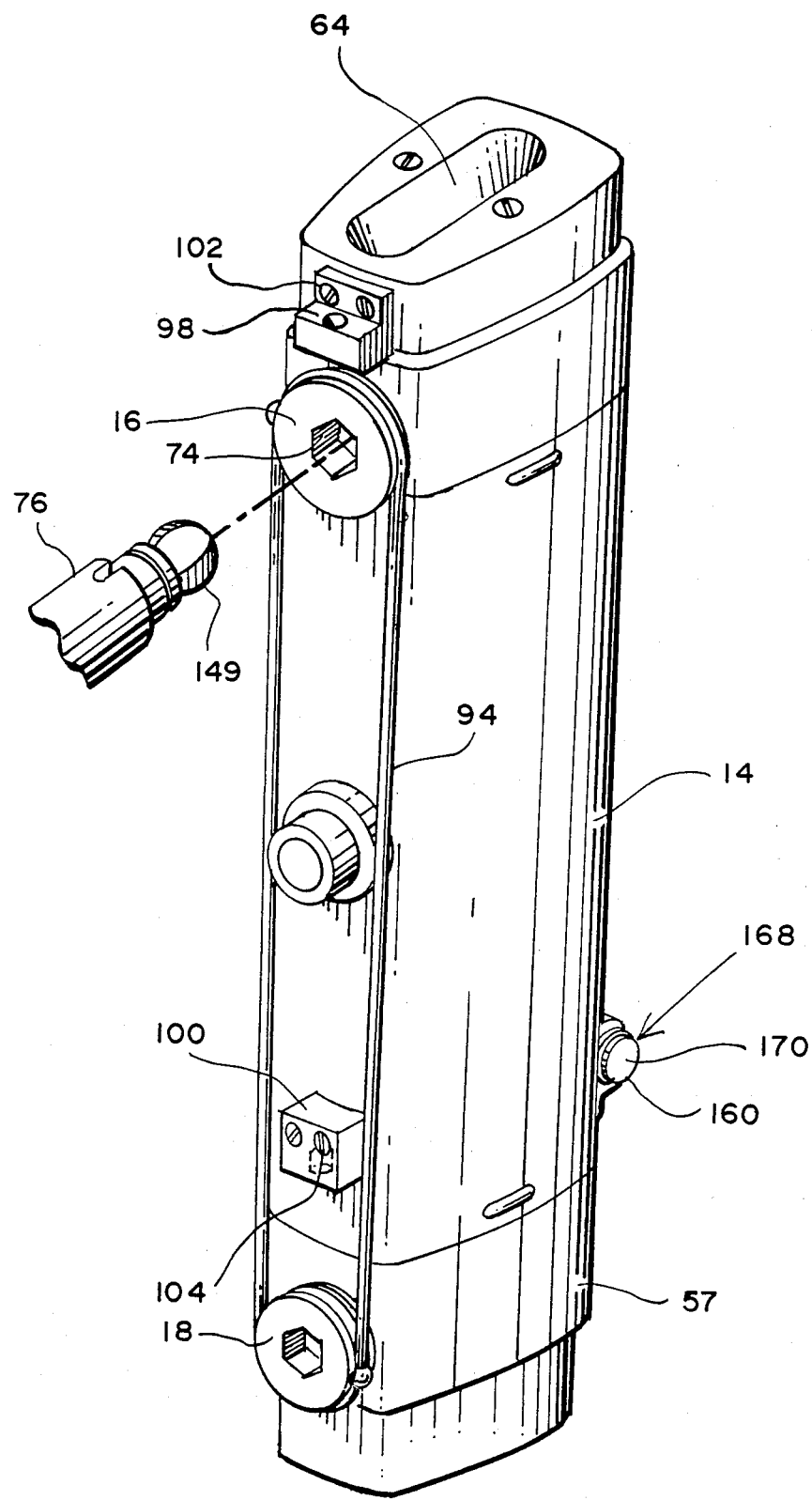
FIG. 7 shows a perspective view of one of the bottles of the present invention.

Referring to FIG. 6, each cylindrical valve 16 contains a main body portion 72 having the pair of apertures 68. A pair of hexagonal shaped cavities 70 and 74 are formed at opposed ends of the cylindrical valves 16 and 18. The cavity 70 can have a tool inserted therein, which can be manually used to rotate the cylindrical valve 16, i.e., to reset the valve. Referring to FIG. 7, the six sided cavity 74 is for receiving a hexangonal-shaped key 76, similar to that disclosed in U.S. Pat. No. 4,593,570. Referring back to FIG. 6, the retainer ring 62 is disposed in a circular slot 80 disposed around the periphery of each end of the valve 16 or 18. The cavities 74 in the valve 18 are unnecessary, since rotation of valve 16 rotates valve 18, as will be described hereinafter.

As can be seen from the top view of the bottle shown in FIGS. 3 and 4, the aperture 64 of the outer seat has a cross-sectional configuration with a straight elongated center portion 82 terminating with opposed semicircular portions 84. The aperture 66 of the inner seat has a matching configuration. The pair of apertures 68 of the valve 16 together generally conform to the configurations of the apertures 64 and 66.

Referring to FIG. 6, the casing 57 has an elongated, circular lower portion 86 which extends downward into the bottle 14 and engages an elongated tubular member 88. In a conventional manner, a plastic monofilament 89 is positioned between matching circular grooves in the lower portion 86 and tubular member 88 to lock the casing 57 to the tubular member 88. Additionally, an O-ring 91 is positioned therebetween.

Referring to FIG. 6, in the preferred embodiment a plastic bag 90 for containing the water sample preferably, but not necessarily, is positioned within the tubular member 88 with its open top being securely mounted between portion 86 and the upper portion of tubular member 88. The cylindrical valve 18 at the other end of the tubular member 88 is identical in construction and operation to the cylindrical valve 16, except the inner seat 66 does not need the elongated portion 86, since the bag 90 is only connected at one end and the cavities 70 and 74 are not needed for rotation. When the casing 57 is removed, the bag 90, with the water sample therein, can be removed. Additionally, the water sampler 10 can work without use of such bag 90.

Referring to FIGS. 6 and 7, the extended portions of the valves 16 and 18 each have a circular groove 92 formed therein for receiving a synchronization chain 94 or like belt means. In this manner, when the upper valve 16 is rotated, the lower valve 18 is rotated by the same number of degrees. In a conventional manner, a hydrostatic, pressure release valve 96 is mounted in the tubular member 88 to equalize pressure.

Figure 9:
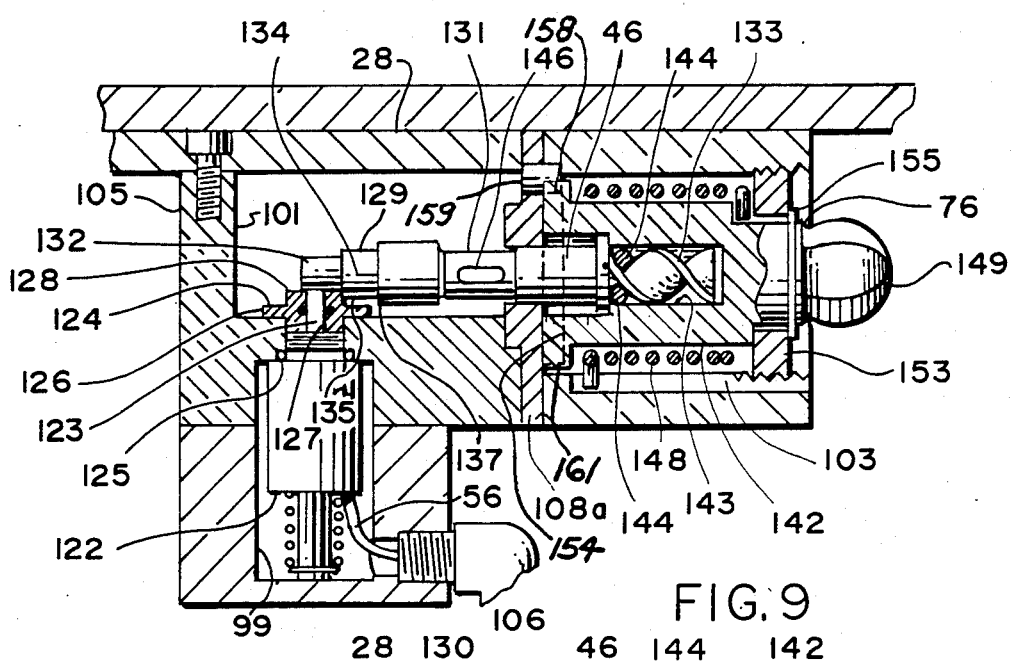
FIG. 9 is a cross sectional view showing the triggering mechanism in its loaded position wherein the cylindrical valve is closed.

Referring to FIGS. 1 and 4, the cross sectional configuration of the bottles 14 have a substantially trapezoidal configuration with round corners. The trapezoidal configuration allows for a short width at one end with outward tapering sides extending therefrom so as to maximize the number of bottles that can be mounted around the circular plates 28 and 30. Referring to FIG. 2, a pair of ledges 98 and 100 are rigidly mounted to the bottles 14 and, by means of screws 102 and 104 respectively, are secured to the plates 28 and 30. The upper portion 42 of housing 38 includes an upper ring portion 105 and a lower ring portion 106. Referring to FIG. 9, cavity 99 is formed in portions 105 and 106 and cavity 101 is formed in portion 105, for housing portions of the mechanism 46. In addition, a cylindrical housing 103 is secured to a plate 108a in a position adjacent the valve 16. The plate 108a is secured to the upper ring portion 105. The housing 103 also contains a portion of the mechanism 46.

Figure 8:
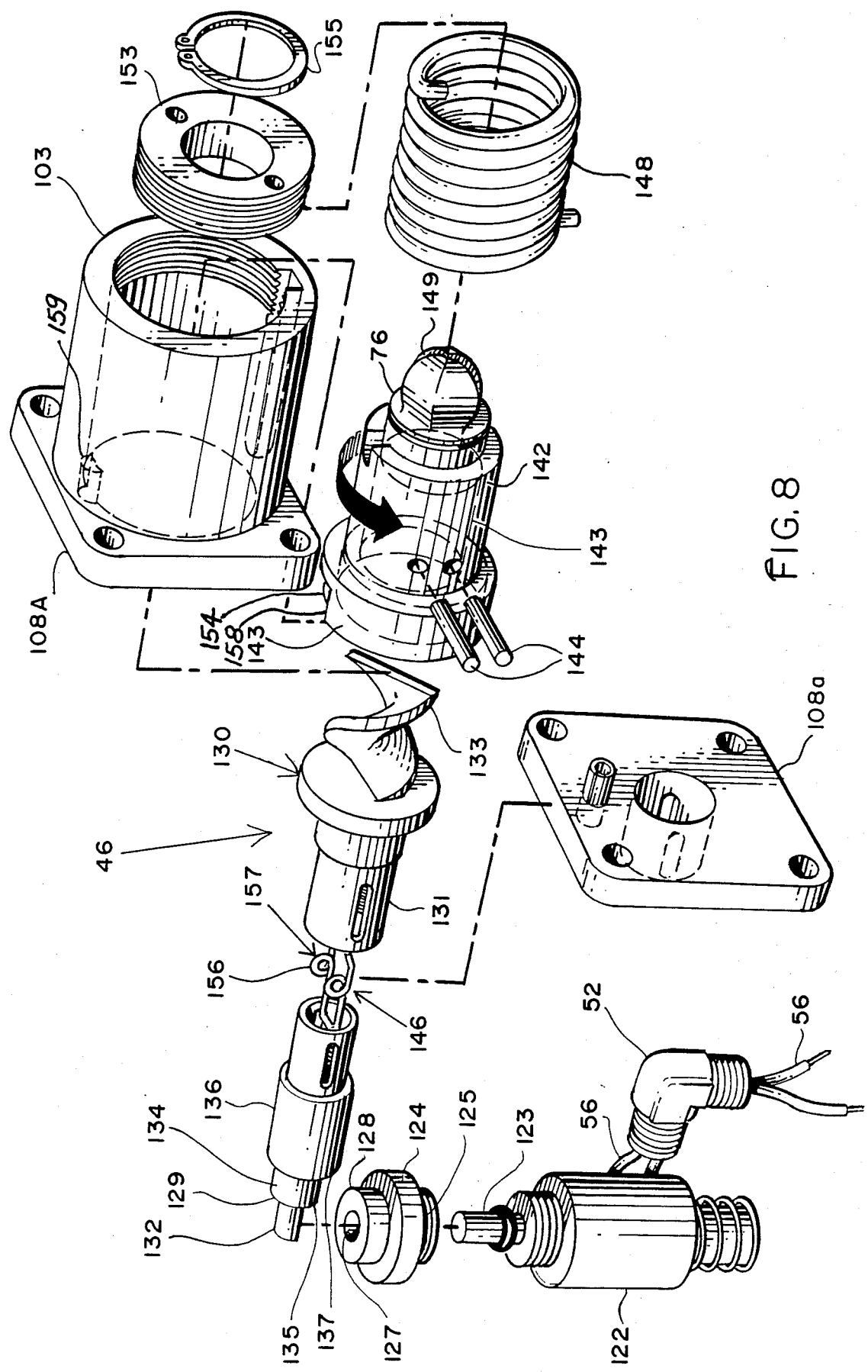
FIG. 8 shows an exploded view of the triggering mechanism of the present invention.

Referring to FIGS. 8 and 9, there is one triggering mechanism 46 for each of the bottles 14. Each of the triggering mechanism 46 includes a solenoid 122 mounted in cavity 99 and which has power provided to it at predetermined times from the power supply and electronic module 44 via the electrical conductors 56. The solenoid has a plunger 123 which extends outward when electrical current is provided to the solenoid. The solenoid 122 used in the preferred embodiment is manufactured by Ledge, Inc. of Vandalia, Ohio (Code Identification No. 81840). Mounted in the bottom of cavity 101 is a floor member 124 which is secured to the ring portion 105 for each solenoid 122. A ring gasket 125 is positioned around each floor member 124. An aperture 127 is formed in the floor member 124 to receive the plunger 123. When the solenoid 122 is in its non-energized state, the upper top of the plunger is level with an upwardly extending portion 128 of the floor member of the 124. When energized, the plunger 123 extends upward above portion 128 to engage a rod member 130. The rod member 130 includes a rotation-stopping portion 129, a center portion 131, and a spiral rod portion 133. At one end of the rod member 130, the rotation-stopping portion 129 has integrally formed therein three parts, consisting of an outer most part 132, a middle part 134, and an inner most part 136. The outer most and middle parts 132 and 134 both have a cutaway portion which defines a flat surface facing downward toward the solenoid. Each of the parts 132 through 136 extend downwardly more than the previous part as one progresses toward the center of the rod member 130. The junction of parts 132 and 134 define a first ledge 135, i.e., first catch means, and the junction of parts 134 and 136 define a second ledge 137, i.e., second catch means. Thereafter, the rod member is made up of the center portion 131 to which the spiral rod portion 133 is rigidly secured thereto. Disposed in surrounding relationship to the spiral rod portion 133 is a rotating member 142 in the form of a push nut. The push nut defines an interior cavity 143 into which the spiral rod portion 133 extends. A pair of guide pins 144 extend through the rotating member 142 in parallel, spaced apart relationship so as to relatively closely fit into the groove formed by the spiral of the spiral rod portion 133. At one end of the member 142 there is formed the key 76 having a hexagonal shaped drive lug 149 formed therein and adopted to engage in cavity 74 of the value 16. A joint 146 is formed in the center portion 131, such joint 146 allowing the end of the rod member 130 having the rotation stopping portion 129 to slightly move upward without affecting the horizontal disposition of the spiral rod portion 133. The spiral rod portion 133 takes the form of a lead screw in the preferred embodiment. A torsion spring 148 is positioned in housing 103 and is disposed in surrounding relationship to the rotating member 142 with one end thereof secured to the rotating member and the other end secured to the housing 103. To provide downward biasing, a spring 156 is mounted between the rotation-stopping portion 129 and the center portion 131 in the joint 146. By way of this biasing force, as will be described hereinafter, whatever portion of the rod member 130 is positioned over the plunger 123, the rod member 130 will abut against the end of the plunger 123. An adjustment nut 153 and retaining clip 155 are positioned over the end of key 76.

With respect to the claims appended hereto, the combination of the solenoid 122 and the spring 156 (i.e., biasing means) define a lateral movement means 157 which ensures sufficient displacement of the end of the rotation-stopping portion 129 to, first, disengage first ledge 135 (i.e., first catch means) from the floor member 124 (i.e., stop means) and then, second, engage the second ledge 137 (i.e., second catch means) with the floor member 124. Thereafter, a repeat energization of the solenoid 122 again causes the disengagement of the second ledge 137 from the floor member 124. It has been found that for both energization that the plunger 123 moving forward by about one-sixteenth of an inch is sufficient.

Figure 10:
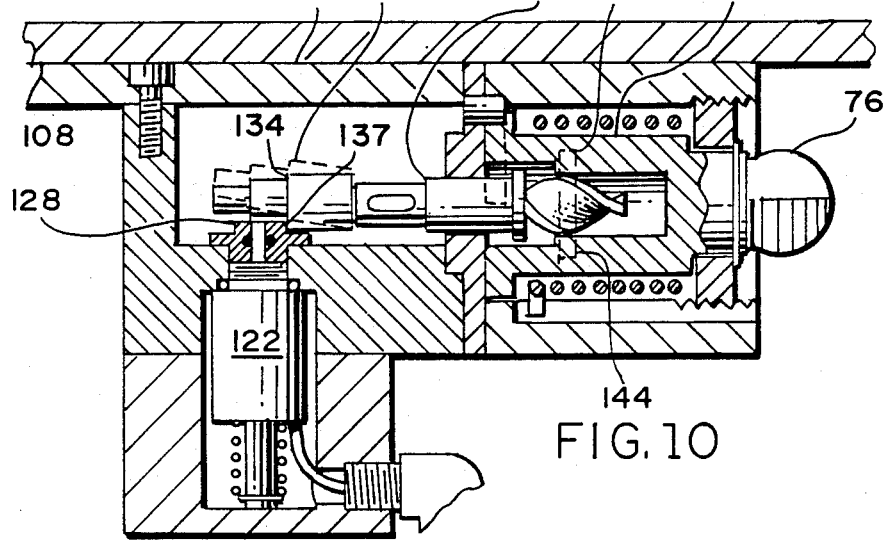
FIG. 10 is a cross sectional view showing the trigger mechanism in its second stop position when the cylindrical valve is in its opened position.
Figure 11:
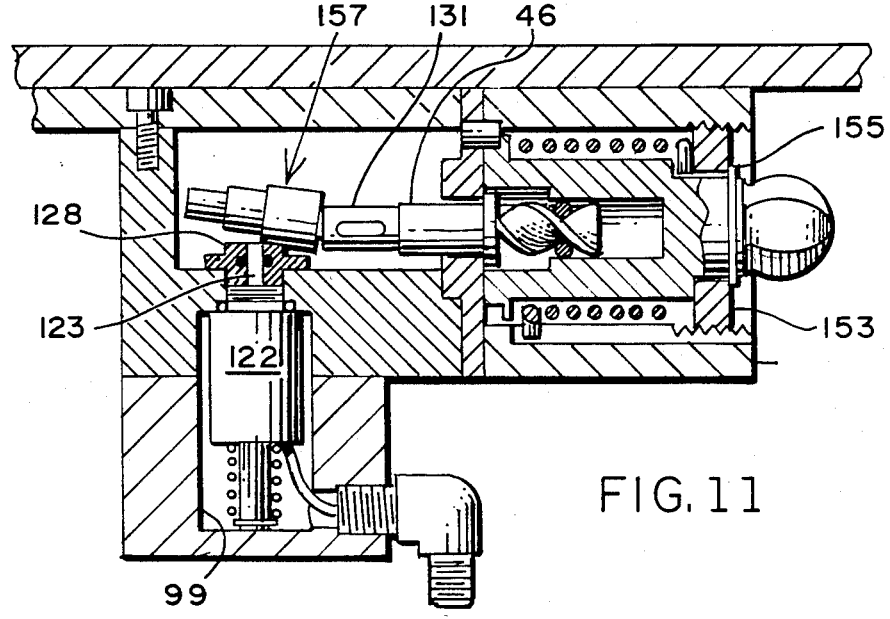
FIG. 11 is a cross sectional view which shows the trigger mechanism in its third stop position when the cylindrical valve is again closed to contain the water sample.

The operation of the triggering mechanism 46 shown in FIGS. 9 through 11, will be described as follows. In the preferred embodiment, the bottles have their cylindrical valves 16 and 18 in their opened position as the device 10 is lowered into the water. However, the other embodiments, they might be initially closed. As shown in FIG. 9, the triggering mechanism 46 is in its loaded position, such position being with the bottles 14 in its initially closed position. In this loaded position (i.e., first stop position) prior to the plunger 123 moving upward, the rod member 130 is prevented from moving along its longitudinal axis due to ledge 135 engaging the upwardly extending portion 128. At a plurality of predetermned depths, the module 44 will activate a plurality of triggering mechanisms 46 so as to obtain a number of water samples, normally one at each predetermined depth. When an initially loaded activating mechanism is triggered, the solenoid 122 is energized and the plunger 123 extends upward into the cavity 101. The upward movement of the plunger 123 causes the rod member 130 to move upward to the extent that the flat surface of center part 134 now is above the upwardly extending portion 128 of the floor member 124. In other words, after the plunger 123 engages the outer most part 132 and pushes it up, the ledge 135 is freed. The torque spring 148 applies a rotational biasing force to the rotating member 142, which was kept in check by the pins 144 prior to the ledge 135 becoming free. After the ledge 135 is freed up, the rod member 130 can move forward toward the radial axis of the holder 12. As the rotating member 142 rotates, the pins 144 also rotate, causing the rod member 130 to advance until the upwardly extending portion 128 of the floor member 124 engages the second ledge 137 (second stop position). As shown in FIG. 10, upon such engagement, again the rod member 130 prevents the rotating member 142 from further rotation. However, the spirals in the spiral rod portion 133 are so designed, that upon advancement of the rod member 130 from the first ledge 135 (first stop position) to the second ledge 137 (second stop position), the rotating member 142 rotates exactly 90°. Since the key 76 is secured to the rotating member 142, the key 76 rotates the cylinder valve 16 by 90° (refer to FIG. 7), changing such cylinder valve 16 from its closed position to its open position to collect a water sample. Likewise, through the chain arrangement interconnecting the lower cylindrical valve 18, the lower cylindrical valve 18 is also rotated 90° to its opened disposition. Providing sufficient time for the water to enter, the solenoid 122 is again energized so that plunger 123 extends out to cause the second ledge 137 to clear the floor member 124. Again, as shown in FIG. 11 the rod member 130 can advance forward due to the biasing force of the torsion spring 148 and comes to rest in a third stop position due to a ledge 158 of the rotating member 142 engaging a pin 159. As can be seen better in FIGS. 8 and 9, the pin 159 is mounted to the housing 103 and moves in a cut-out 154 formed in member 142, with the cut-out defining a pair of opposed ledges 158 and 161 which prevents rotation of more than 180 degrees in both directions. When the torsion spring 148 has fully unwound, then the rotating member 142, and therefore valves 16 and 18, will have rotated another 90°, so as to move the valves from their opened position to their closed position. During the entire operation the valves 16 and 18 rotate 180°.

Figure 12:
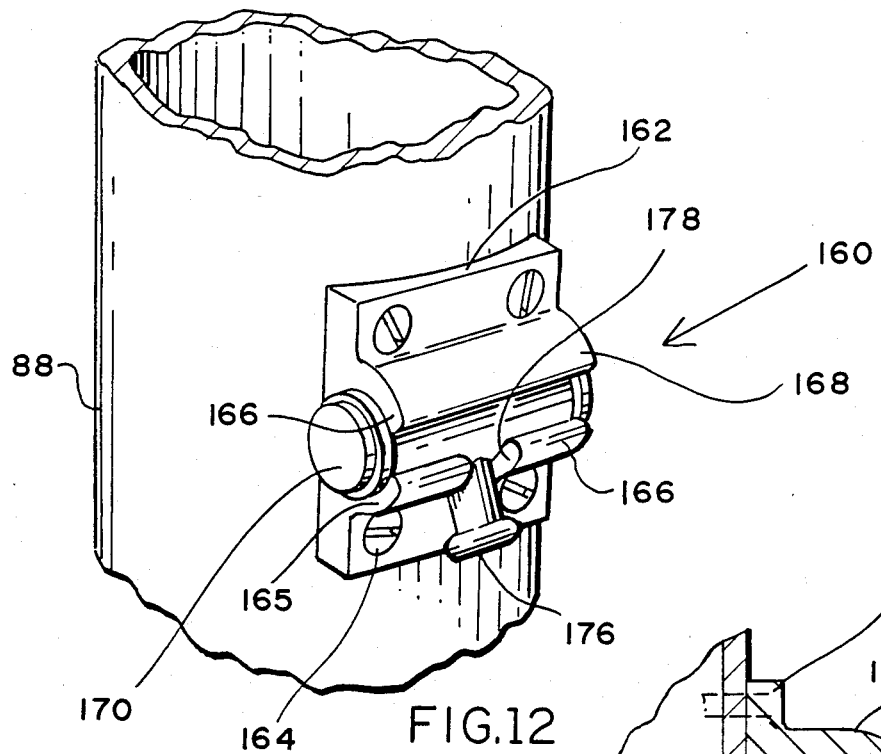
FIG. 12 is a perspective view of the drain valve of the present invention.
Figure 13:
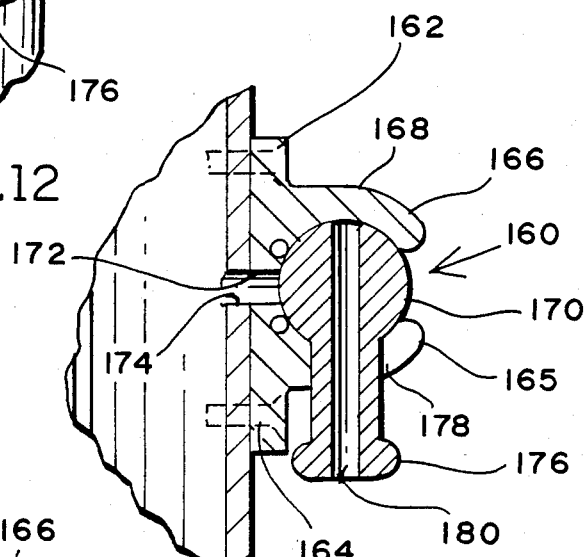
FIG. 13 is a cross sectional view of the drain valve of the present invention in its closed disposition.
Figure 14:
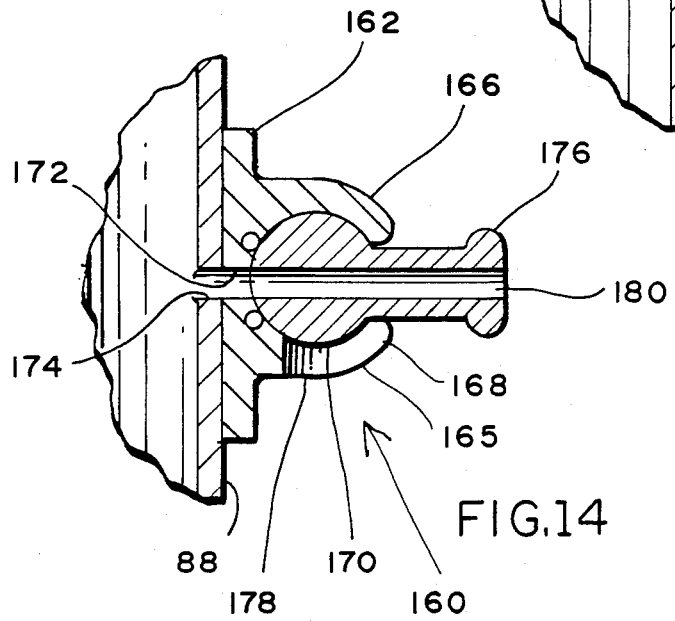
FIG. 14 is a cross sectional view of the drain valve of the present invention in its opened disposition.

As shown in FIGS. 12 through 14, a flush or drain valve 160 is provided for flushing or draining the bottle 14. The drain 160 includes a rectangular base member 162 which is secuted to the tubular member 88 by a plurality of screws 164. Integrally formed on the base portion 162 is two curvilinear portions 165 and 166 which together define a partial sleeve 168 to rotatable contain a cylinder member 170. The base member 162 has a hole 172 formed therein which is disposed over a hole 174 formed in the tubular member 88. A handle 176 is mount on and extends outward from the cylinder member 170. A cut-out notch 178 is formed in the curvilinear portion 165 for receiving the handle 176. A bore hole 180 is disposed through handle 176 and the cylinder member 170. When the handle 176 extends outward at right angles to the tubular member 88, the center axes of holes 172, 174 and 180 are coincident and a unrestrained path is provided for the drainage of the water sample contained in the bottle 14. As the handle 176 is rotated upward, then the path for, and therefore the flow of, liquid is progressively restricted until the entire flow is cut off. In this manner, the rate of flow is adjustable. Additionally, the handle 176 has dual purposes of being both a means for rotating the cylinder member 170 and providing a spout for the liquid flowing through the drain 160.

Figure 15:
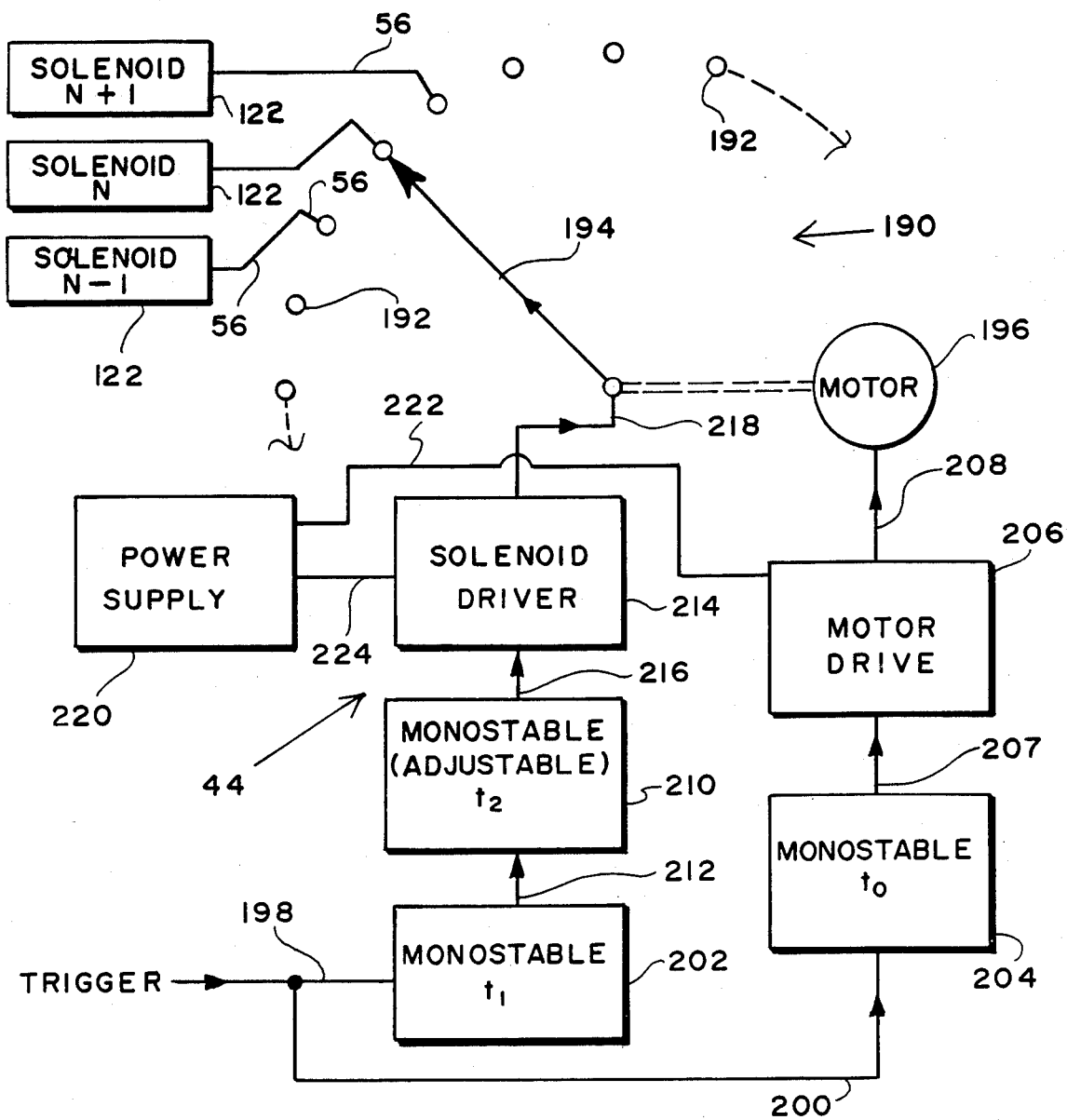
FIG. 15 is a schematic diagram of the electrical circuits for sequentially activating solenoids.
Figure 16:
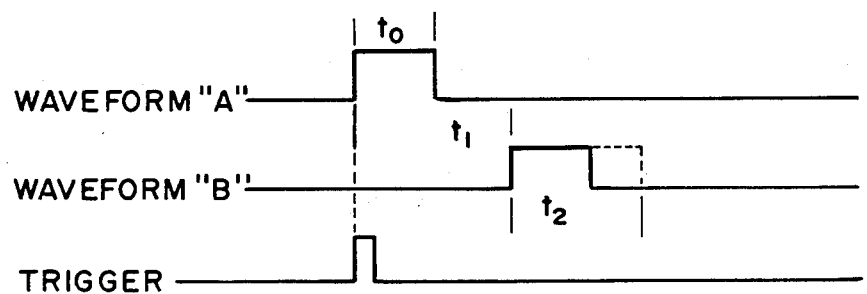
FIG. 16 shows the signals as generated in the circuitry of FIG. 15.

Referring to FIG. 15, the power supply and electronic module 44 is shown wherein conventional circuitry arrangements can be readily modified to activate and deactivate the plurality of triggering mechanisms 46. For example, as shown in FIG. 15, a conventional rotary switch 190 is used with the preferred implementation of the triggering mechanisms 46. Switch 190 has a plurality of contacts 192 (only partially shown in the FIG. 15) disposed in a circle and equal in number to the number of mechanisms 46. Each contact 192 is electrically connected to one of the solenoids 122 of one of the mechanisms 46 via electrical connectors 56. Although not required, the mechanisms 46 are progressively connected in the same order as the contacts 192. For the purposes of illustration, only three solenoids 122 are shown and are labeled N−1, N, and N+1. The switch 190 includes a rotating contact arm 194 which electrically engages successively each of the contacts 192 as the contact arm 194 completes a complete circle. A stepping motor 196 is used to rotate the contact arm 194. Preferably, but not necessarily, the stepping motor 196 and its associated circuitry is located in the holder 12. Through a push button signal generating source (not shown) located, for example, on a ship, a "trigger" signal is applied via electrical conductors contained in power cable 20 through electrical path 198 and 200 to a pair of monostable devices 202 and 204, respectively. The monostable device 204 generates an activating signal provided to a motor drive 206 via electrical path 207, such activating signal having a duration $t_0$. In response thereto, the motor driver 206 energizes the motor 196 over electrical path 208 for a period of time having a duration of $t_0$, as shown by waveform "A" in FIG. 16. When so energized, the motor 196 steps the switch 190 to the next successive contact 192, which in turn is electrically coupled to the next successive mechanism 46. Upon receiving the trigger signal, the monostable device 202 generates a signal for a duration of $t_1$ to a third monostable device 210 via electrical path 212. Upon receipt of the trailing edge of the signal from device 202, the monostable device 210 sends an activating signal to a solenoid driver 214 via an electrical path 216 for a duration of $t_2$ as shown by waveform "B" in FIG. 16. This in turn causes the solenoid driver 214 to energize via electrical path 218 the appropriate solenoid connected via contact arm 194. The monostable device 210 is such that duration $t_2$, e.g., 100 milliseconds, can be adjusted so that the solenoid is energized for a sufficient period of time to assure movement of the mechanism 46 to clear one of its catches. The solenoid driver 214 and motor driver 206 act as switches to the supply of power 220, which is connected to the solenoid driver 214 and motor driver 206 via electrical paths 222 and 224. When activated by devices 210 and 204, drivers 214 and 206, respectively, energize solenoids 122 and motor 196 with power provided by the power supply 220. In the preferred embodiment, the power supply 220 is located on the surface, for example, on a ship and electrical conductors 222 and 224 are inside of cable 20. Alternatively, the power supply can be located in module 44, in which case it comprises a battery. Additionally, although not normally desirable, for selected applications it is contemplated that triggering mechanisms 46, and therefore bottles 14, can be user selected in a random manner by modifying the electronics of module 44.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. In a water sampler device including a holder, a plurality of water-collecting containers mounted to said holder, each of said water-collecting containers having a pair of opposed open portions, a pair of rotatable valves with one of said pair of rotatable valves being disposed in each of said open portions, means for interconnecting said rotatable valves so that rotation of one of said rotatable valves rotates the other said rotatable valve, triggering means for rotating said rotatable valves from an initially closed condition to an opened condition and then back to said closed condition to collect a sample of water, the improvement in said triggering means comprising:

rod means including a rotation-stopping portion having a first longitudinal axis and further having a first catch means and a second catch means formed therein with said second catch means being disposed a greater distance from one end of said rod means and a greater distance from said first longitudinal axis than said first catch means, said rod means further having a spiral rod portion with a second longitudinal axis;

a rotatable member having a rotational axis and being disposed in surrounding relationship to at least a part of said spiral rod portion with said second longitudinal axis of said spiral rod portion being substantially coincident with said rotational axis of said rotatable member, said rotatable member having traversing means for engaging said spiral rod portion to cause displacement of said spiral rod portion along said rotational axis when said rotatable member is rotated;

torsion means connected between said holder and said rotatable member for applying a torque to said rotatable member;

stop means mounted to said holder for engaging said first catch means in a first stop position to prevent longitudinal movement of said rod means along said first longitudinal axis and for engaging said second catch means in a second stop position to prevent longitudinal movement of said rod means;

lateral movement means mounted to said holder for causing said rotation-stopping portion to move laterally with respect to said first longitudinal axis to disengage said stop means from said first catch means in said first stop position and to engage said stop means with said second catch means in said second stop position and thereafter to disengage said stop means from said second catch means so as to allow said rod means to move to a third stop position; and coupling means for coupling said rotable member to one of said rotatable valves so that rotation of said rotatable member permitted by longitudinal movement of said rod means between said first stop position and said second stop position allows for said rotatable member to rotate said rotatable valves from said closed condition to said open condition and rotation of said rotatable member permitted by longitudinal movement of said rod means between said second stop position to said third stop position allows for said rotatable member to rotate said rotatable valves from said opened condition to said closed condition.

2. The water sampler device according to claim 1, wherein said first catch means comprises a first ledge formed in said rotation-stopping portion and substantially disposed in a first plane perpendicular to said longitudinal axis and said second catch means comprises a second ledge formed in said rotational-stopping portion and substantially disposed in a second plane perpendicular to said longitudinal axis.

3. The water sampler device according to claim 2, wherein said lateral movement means includes a solenoid having a plunger, said plunger when activated being disposed to engage said rotation-stopping portion at an angle to said first longitudinal axis and to cause movement of said rotation-stopping portion in a direction away from said stopping means, said lateral movement means further includes a biasing means to bias said rotation-stopping means in a direction opposite to said movement caused by said plunger and to limit said movement to a predetermined distance, whereby said movement of said rotation stopping portion by said predetermined distance causes said stop means to be disengaged from said first ledge and to engage in stopping relationship said second ledge and thereafter to disengage from said second ledge.

4. The water sampler device according to claim 3, wherein said stopping means comprises a protrusion mounted to said holder adjacent to said plunger, said protrusion defining a third ledge, said third ledge being disposed to engage said first and second ledges.

5. The water sampler device according to claim 1, wherein said spiral rod portion comprises a lead screw.

6. The water sampler device according to claim 1, further including a center portion disposed between said rotation stopping portion and said spiral rod portion, said center portion including joint means for allowing said first longitudinal axis to be angled with respect to said second longitudinal axis.

7. The water sampler device according to claim 1, wherein said rotatable member comprises a cylinder with a cavity formed therein, said cavity containing said at least a part of said spiral rod portion, and said traversing means comprising a pair of spaced-apart parallel pins secured to said cylinder and disposed in traversing relationship through said cavity to engage opposed sides of said spiral rod portion.

8. The water sampler device according to claim 1, wherein said torsion means comprises a spring.

9. The water sampler device according to claim 1, wherein said lateral movement means includes a solenoid having a plunger, said plunger when activated being disposed to engage said rotation-stopping portion at an angle to said first longitudinal axis and to cause movement of said rotation-stopping portion in a direction away from said stopping means, said lateral movement means further includes a biasing means to bias said rotation-stopping means in a direction opposite to said movement caused by said plunger and to limit said movement to a predetermined distance.

10. The water sample device according to claim 1, wherein said rotatable valve has a valve axis of rotation, said coupling means comprising a key with a key longitudinal axis, said key at one end to said rotatable member and being disposed to removably engage said rotatable valve at the other end.

11. The water sampler device according to claim 10, wherein said valve comprises a cylindrical valve.

12. In a water sampler device including a holder, a plurality of water-collecting containers mounted to said holder and disposed in side by side relationship in a circle around said holder, each of said water-collecting containers having a pair of opposed open portions, each of said open portions having a rotatable valve mounted therein, the improvement comprising:

each of said water-collecting containers having a substantially trapezoidal configuration defining a pair of opposed inwardly-angled sides and a pair of opposed end sides consisting of an inner end side and an outer end side, said inner end side being shorter than said outer end side;

each of said water-collecting containers having four corners defined by said trapezoidal configuration, each of said corners being rounded; and each of said water-collecting containers being disposed in wedged side-by-side relationship around said holder with said inwardly-angled sides of each said water-collecting containers being in abutting relationship with said inwardly-angled sides of other said water-collecting containers.

13. The water sampler device according to claim 12, wherein each of said water-collecting containers includes a chamber-containing member having a first aperture formed therein and a drain valve; said drain valve including a rotatable cylindrical member, means mounted to said chamber-containing member for rotatably securing said cylindrical member, a handle member mounted in protruding relationship on said cylindrical member, and a second aperture formed through said cylindrical member and through said handle member along the longitudinal dimensions of said handle member; and said first aperture and said second aperture being disposed in aligned relationship when said handle is disposed in protruding relationship to said chamber-containing member, whereby said handle member serves the dual purpose of rotating the cylindrical member and being a spout and the extent of rotation of said rotatable member varies the extent of fluid restriction of said first aperture.

14. The water sampler device according to claim 13, wherein said means for rotatably securing said cylindrical member comprises a partial sleeve with notch formed therein to receive said handle member.

15. The water sampler device according to claim 13, further including a plastic bag disposed inside said chamber-containing member.

16. The water sampler device according to claim 12, further including a plastic bag disposed inside each of said water-collecting containers; said plastic bag having an opened end portion secured to said water-collecting containers.

17. The water sampler device according to claim 16, wherein said water-collecting container includes a chamber-containing member, a pair of seat means rotatable secured at opposed ends of said chamber-containing member and containing said rotatable valves, one of said seat means having a downwardly-extending portion extending into said chamber-containing member, said opened end portion of said plastic bag being secured between said chamber-containing member and said downwardly-extending portion.

* * * * *